United States Patent [19]

Hasson

[11] Patent Number: 5,628,757

[45] Date of Patent: May 13, 1997

[54] SURGICAL INSTRUMENT FOR HOLDING A NEEDLE

[76] Inventor: Harrith M. Hasson, 2043 N. Sedgwick, Chicago, Ill. 60614

[21] Appl. No.: 348,775

[22] Filed: Dec. 1, 1994

Related U.S. Application Data

[63] Continuation-in-part of Ser. No. 879,604, May 7, 1992, Pat. No. 5,250,056, and a continuation of Ser. No. 61,324, May 13, 1993, abandoned, which is a continuation of Ser. No. 830,681, Feb. 4, 1992, abandoned, said Ser. No. 879,604, is a continuation-in-part of Ser. No. 830,681.

[51] Int. Cl.$^6$ ............................................. A61B 17/00
[52] U.S. Cl. .......................... 606/148; 606/139; 606/205; 606/207
[58] Field of Search .................... 606/139, 144, 606/147, 148, 151, 176, 205–208, 210–211, 1

[56] References Cited

U.S. PATENT DOCUMENTS

| | | | |
|---|---|---|---|
| D. 275,790 | 10/1984 | Marlowe | 606/207 |
| 439,910 | 11/1890 | Truax | 606/147 |
| 532,306 | 1/1895 | Brown | 606/147 |
| 791,322 | 5/1905 | Clayton | 606/147 |
| 905,007 | 11/1908 | Sether | 606/147 |
| 1,261,586 | 4/1918 | Meeker | 606/147 |
| 1,704,992 | 3/1929 | Sanders | 606/147 |
| 2,597,394 | 6/1952 | Snowden | 606/147 |
| 3,120,847 | 2/1964 | Cavaness | 606/147 |
| 3,277,895 | 10/1966 | Johnson | 606/205 |
| 3,921,640 | 11/1975 | Freeborn | 606/207 |
| 4,452,106 | 6/1984 | Tartaglia | 606/210 |
| 4,793,349 | 12/1988 | Weinrib | 606/148 |
| 4,896,678 | 1/1990 | Ogawa | 128/751 |
| 4,935,027 | 6/1990 | Yoon | 606/148 |
| 4,944,741 | 7/1990 | Hasson | 606/206 |
| 4,961,742 | 10/1990 | Torre | 606/147 |
| 5,015,250 | 5/1991 | Foster | 606/148 |
| 5,100,421 | 3/1992 | Christoudias | 606/147 |
| 5,300,082 | 4/1994 | Sharpe et al. | 606/147 |

FOREIGN PATENT DOCUMENTS

| | | | |
|---|---|---|---|
| 0065054 | 12/1981 | European Pat. Off. | 606/205 |
| 0416689 | 7/1925 | Germany | 606/147 |
| 677726 | 7/1939 | Germany | 606/148 |
| 3048758 | 7/1982 | Germany | 606/205 |
| 2091624 | 8/1982 | United Kingdom | 606/205 |
| 2210574 | 6/1989 | United Kingdom | 606/207 |

*Primary Examiner*—Jeffrey A. Schmidt
*Attorney, Agent, or Firm*—Wood, Phillips, VanSanten, Clark & Mortimer

[57] ABSTRACT

A surgical instrument for holding a needle, which instrument has first and second elongate jaws movable selectively towards and away from each other between a) an open position in which a needle can be placed between the jaws and b) a closed position in which the jaws can captively embrace a needle. A structure, and preferably a sleeve, is movable lengthwise relative to and against at least one of the first and second jaws between first and second positions to thereby move the jaws between their open and closed positions. There is a seat on one of the first and second jaws for reception of a needle to be held by the surgical instrument and a cam surface on the other of the first and second jaws for wedging a needle in the needle seat in the one of the first and second jaws as an incident of the jaws being moved from their open position into their closed position to thereby positively hold a needle in an operative position on the needle holding instrument. The camming action between the cooperating jaws positively holds the needle in its operative position.

19 Claims, 5 Drawing Sheets

SURGICAL INSTRUMENT FOR HOLDING A NEEDLE

CROSS REFERENCE

This application is a continuation-in-part of application Ser. No. 07/879,604, filed on May 7, 1992 and issued as U.S. Pat. No. 5,250,056, which application in turn is a continuation-in-part of application Ser. No. 07/830,681, filed Feb. 4, 1992 (now abandoned). This application is also a continuation of application Ser. No. 08/061,324, filed May 13, 1993 (now abandoned), which is a continuation of application Ser. No. 07/830,681, now abandoned.

BACKGROUND OF THE INVENTION

1. Field of the Invention

This inventions relates to surgical instruments and, more particularly, to an instrument for holding a needle to facilitate manipulation of that needle as during suturing.

2. Background Art

There are several different types of needle holders currently available on the market. In open surgical procedures, it is known to hold a needle with an instrument that operates much like a pair of conventional pliers. The user can squeeze a pair of handles with or without a locking mechanism thereon with a force that dictates the gripping force on the needle. This type of instrument has several drawbacks. First of all, it is not suitable for the performance of suturing using laparoscopic techniques, due to its size and the amount of space required to effect operation thereof. Another drawback with this type of device is that if the needle holder is modified to accommodate the small space requirement of laparoscopy, as by making the jaws in the form of an alligator forceps, the amount of mechanical force available with the smaller pivoted jaws may not be sufficient to hold the needle securely and the needle can be easily displaced or dropped by the user. Furthermore, laparoscopic suturing often requires awkward positioning of the user's hand and subsequent transmission of the force applied against the needle along unfavorable lines. This may result in the inadvertent torquing or escape of needle from the instrument. Laparoscopic suturing requires a needle holder with a trapping mechanism that allows the needle to remain stable and securely within the device, regardless of the amount or direction of force applied during a procedure.

Figure 9:
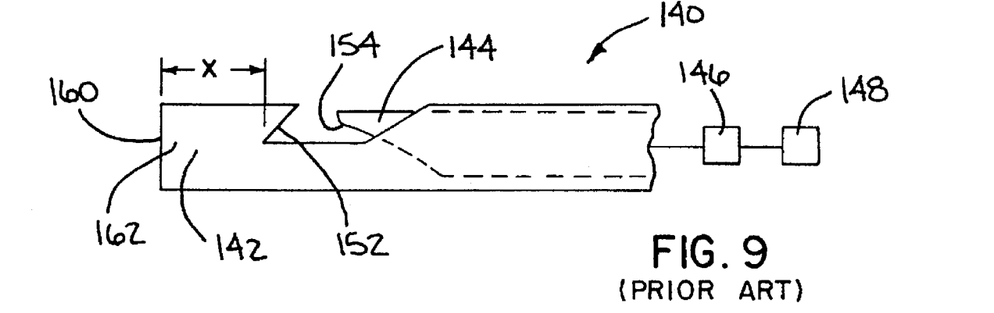
FIG. 9 is a fragmentary side elevation view of the needle holding portion of a prior art surgical instrument with the instrument shown in an open position.
Figure 10:
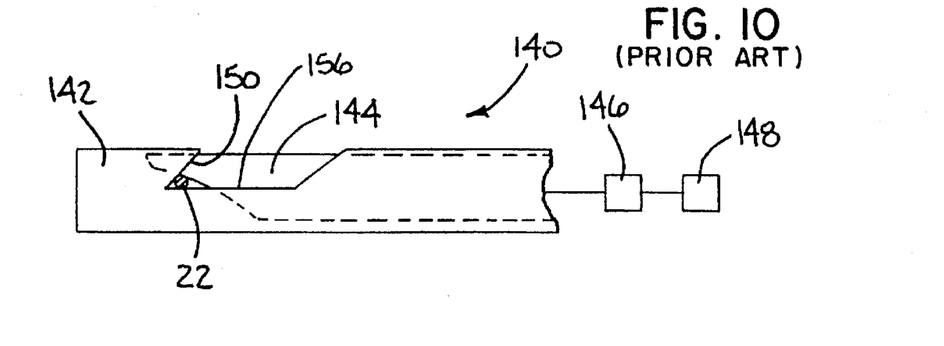
FIG. 10 is a view as in FIG. 9 with the instrument in a closed position.

One commercially available instrument overcomes the above problems. This device is currently being sold by Cook Urological and is identified as its "Endoscopic Curved Needle Driver". This instrument has a pistol-type grip for actuation and has a needle holding mechanism, as shown in FIGS. 9 and 10 of the present application. The instrument has an outer sleeve with a cut-out therein defining a V-shaped, rearwardly opening seat for a needle. The needle seat is spaced a substantial distance away from the free distal end of the outer sleeve. An inner sleeve, concentric with the outer sleeve, is biased towards the front of the instrument. The inner sleeve has a blocking edge that is angularly disposed with respect to the axis of the inner sleeve and in moving forwardly through the slot in the outer sleeve, captively wedges the needle into the seat defined in the outer sleeve. The bias from the inner sleeve is sufficient by itself to hold the needle securely in an operative position allowing suturing to be performed. This allows the user to concentrate solely on manipulation of the instrument.

The latter device has a number of drawbacks. Most notable of these drawbacks is the location of the needle seat, which is spaced substantially away from the free distal end of the outer sleeve. This arrangement makes it impossible for the user to direct the instrument lengthwise of a needle to effect operative engagement therewith. For example, if a needle were to escape from the instrument, the user would have to reposition the instrument, possibly at a severe angle, to allow the needle to re-enter the cut-out and re-seat.

A further drawback with the latter device is that the gripping force on the needle is dictated by the structure which biases the inner sleeve in a forward direction. In the event that the spring force decreases, as may occur over time, the gripping force on the needle may diminish to the point that the instrument may need to be reconstructed or discarded.

A further disadvantage with the latter device is that it is capable of holding the needle, and particularly a curved needle, in only one orientation. This necessitates the construction of several different models to accommodate left- and right-handed persons as well as limiting the versatility of each such model.

A still further drawback with the latter device is that the needle, in its operative position, is situated a substantial distance behind the free distal end of the instrument. As a result, the portion of the outer sleeve that is forwardly of the position of the needle acts as an obstruction which may block the performance of certain suturing procedures. This leading portion has to be pushed into the tissues or otherwise moved out of the way to place the instrument at an awkward angle, before the sharp point of the needle can be presented at the leading edge of the tissue to be sutured.

A still further problem with the latter device is that the cut-out, through which the needle must be introduced, is small and is positioned on one side of the sleeve, thereby creating a blind spot on the other side. Therefore, the cut-out is not always readily visible to the user during laparoscopic procedures. The user may be required to blindly search for the cut-out and may be required to constantly rotate the needle to locate the needle in the cut-out to seat the needle in its operative position. This complicates the surgical procedure and may undesirably prolong the same as the user continuously releases and re-grips a needle as occurs during the normal suturing process.

SUMMARY OF THE INVENTION

The present invention is specifically directed to overcoming the above-enumerated problems in a novel and simple manner.

More particularly, the present invention is directed to a surgical instrument for holding a needle, which instrument has first and second elongate jaws movable selectively towards and away from each other between a) an open position in which a needle can be placed between the jaws and b) a closed position in which the jaws can captively embrace a needle. A structure, and preferably a sleeve, is movable lengthwise relative to and against at least one of the first and second jaws between first and second positions to thereby move the jaws between their open and closed positions. There is a seat on one of the first and second jaws for reception of a needle to be held by the surgical instrument and a cam surface on the other of the first and second jaws for wedging a needle in the needle seat in the one of the first and second jaws as an incident of the jaws being moved form their open position into their closed position to thereby positively hold a needle in an operative position on the needle holding instrument. The camming action between the cooperating jaws positively holds the needle in its operative position.

The jaws each have a proximal end and a distal end. In the open jaw position, there is an unimpeded path for a needle moving lengthwise of the jaws in a direction from the distal end towards the proximal end of the jaws to between the jaws.

With the above structure, the jaws can be directed lengthwise to position the jaws over a needle to conveniently pick the same up and move it into its operative position without close visual monitoring of the jaws. The spacing between the distal ends of the open jaws defines the pickup range for the instrument. With known technology, this range can be made quite large in a highly compactible structure. By providing two cooperating sets of jaws, the effective pickup space is circular with a diameter equal to the spacing of the distal ends of the open jaws. The user thus does not have to concentrate on the angular orientation of the jaws to line the jaws up with the needle to effect pickup thereof.

To provide a positive grip on a needle in its operative position, the seat has a curved surface opening in a first direction and the cam surface faces oppositely to that first direction. In one form, the seat opens rearwardly and radially inwardly relative to the axis of the sleeve. The surface may be square, V-shaped, U-shaped, or otherwise configured to define a conforming receptacle for a needle.

In a preferred form, the needle in its operative position is situated closely adjacent to the forward edge of the sleeve. In one form, the needle is drawn by the jaws forcibly against the forward edge of the sleeve so that the sleeve and jaws cooperatively and positively hold the needle in its operative position. At the same time, the needle in its operative position remains conveniently close to the front of the instrument to facilitate suturing in even tight spaces.

The invention also contemplates a surgical instrument for holding a needle and having a body with first and second jaws integrally formed with the body, which jaws are selectively movable between open and closed positions.

The jaws are preferably closed by a sleeve which surrounds the jaws and is movable between first and second positions. An actuator normally biases the sleeve into one of the first and second positions therefor.

The actuator has a hand grip including a first member connected to the body and a second member connected to the sleeve, with the second member being movable relative to the first member to effect movement of the sleeve between its first and second positions. A spring-type element acts between the first and second members to normally bias the jaws into one of the open and closed positions.

In one convenient form, the grip is a pistol-type grip defined by a U-shaped element with a base and spaced legs. The legs define the first and second members. The legs are graspable in the hand of the user.

In a structure in which the sleeve is normally biased to close the jaws, the user can conveniently squeeze the hand grip, locate the needle for gripping by the instrument, and release the grip so that the instrument automatically grips and holds the instrument positively in its operative position without the user's assistance.

The invention also contemplates structure for enhancing the grip by the jaws. This allows the user to preliminarily place the needle in its operative position and thereafter make an adjustment to more positively grip the needle.

The invention also contemplates a surgical instrument for holding a needle and having first and second jaws movable between open and closed positions, with structure on the jaws for holding the needle selectively in first and second positions, with the first and second needle positions being substantially perpendicular to each other.

In one form, the jaws have facing surfaces which cooperatively embrace a needle with the needle in the first needle position. There is a recess in one of the first and second jaws defining a seat for situation of the needle in the second needle position.

The invention further contemplates a surgical instrument for holding a needle having first and second jaws, movable between open and closed positions, with structure for biasing the jaws into their closed position with a first predetermined force and a second structure for selectively biasing the jaws into the closed position with a force that is greater than the first predetermined force.

In one form, a first sleeve provides the first predetermined biasing force and a separate, second sleeve provides the biasing force that is greater than the first predetermined force.

DETAILED DESCRIPTION OF THE DRAWINGS

Figure 1:
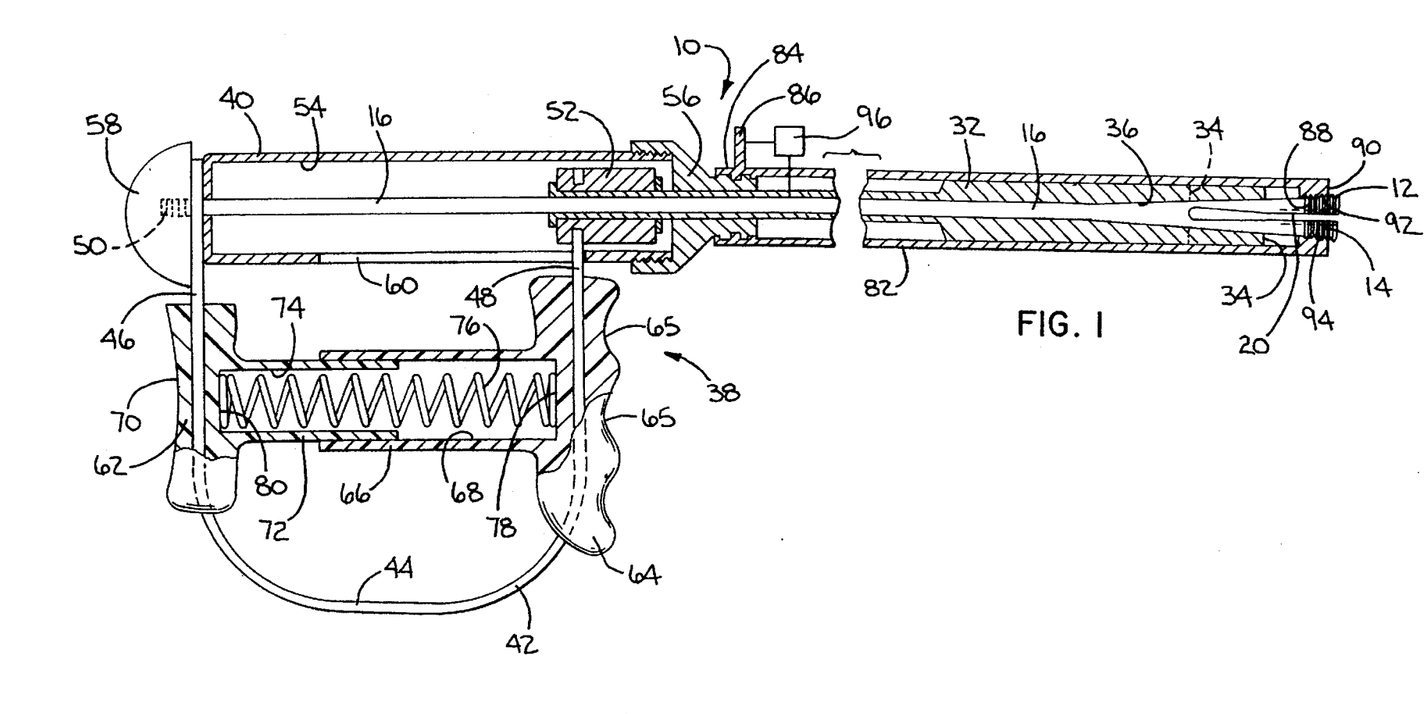
FIG. 1 is a sectional view of a surgical instrument for holding a needle according to the present invention.
Figure 2:
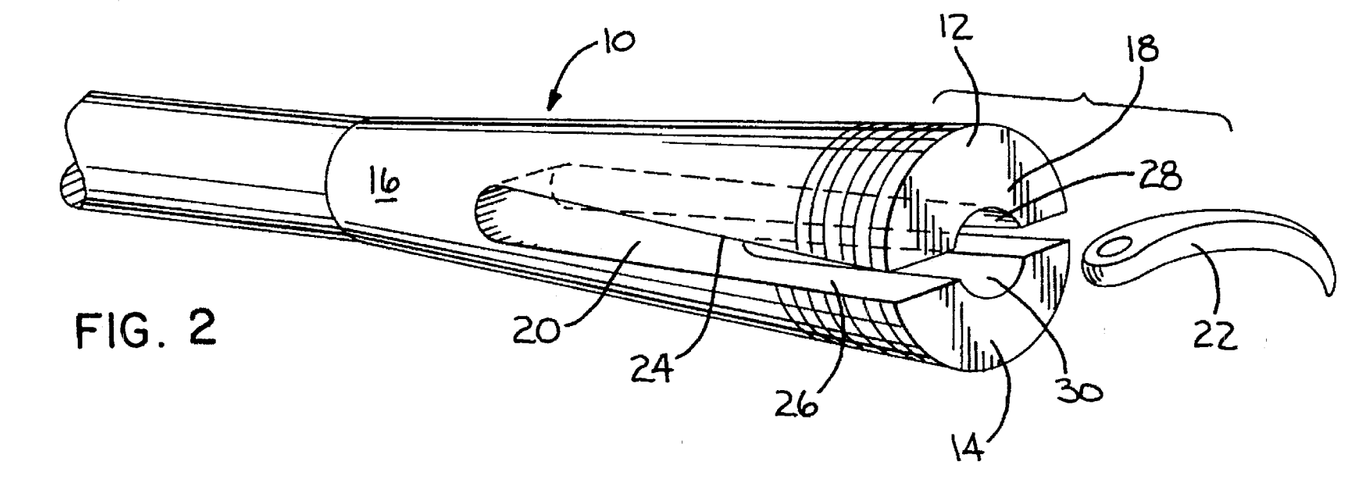
FIG. 2 is an enlarged perspective view of a needle holding portion on the surgical instrument in FIG. 1.

In FIGS. 1 and 2, one form of surgical instrument for holding a needle according to the present invention is shown at 10. The needle holding instrument 10 has first and second elongate jaws 12, 14, integrally formed with and projecting in cantilever fashion from a cylindrical body 16. The jaws 12, 14 have a modicum of flexibility to allow them to move between the open position of FIG. 2 and the closed position of FIG. 1. In the former position, an unimpeded path is defined at the free distal end 18 of the instrument 10 to a space 20 between the jaws 12, 14 to allow the introduction of a suturing needle 22. The needle 22, which is shown to be curved, may have any of a number of different configurations i.e. straight.

The space 20 is bounded by substantially flat surfaces 24, 26 on the jaws 12, 14, respectively. As the jaws 12, 14 are moved towards each other to the closed position, the needle 22 is captively held therebetween. The needle 22 can be held in a number of different positions by the flat surfaces 24, 26. In one preferred orientation, the needle 22 projects laterally away from the jaws, 12, 14 i.e. perpendicular to the length thereof.

To facilitate holding of a needle for projection forwardly from the jaws 12, 14, undercuts/recesses 28, 30 are provided in the jaws 12, 14, respectively. The recesses 28, 30 cooperatively define a seat for the needle 22 to project forwardly, as in the modified structure shown in FIG. 3.

With the jaws 12, 14 fully exposed, the jaws 12, 14 are normally biased away from each other to their open position of FIG. 2. To move the jaws 12, 14 from the open position of FIG. 2 to the closed position of FIG. 1, a stepped sleeve 32 is provided. The sleeve 32 surrounds the body 16 and is movable lengthwise selectively between first and second positions. The first sleeve position is shifted to the left from the solid line position shown in FIG. 1 so that the free end 34 of the sleeve 32 is located as shown in dotted lines in FIG. 1. In the second sleeve position, the free sleeve end 34 is situated in the solid line position of FIG. 1 so that the inside surface 36 captively embraces the jaws 12, 14 and thereby squeezes them towards each other to diminish the space 20 therebetween and thereby captively hold the needle 22. As the sleeve 32 shifts from its first position into its second position, the sleeve 32 progressively biases the jaws 12, 14 to their closed position.

The sleeve 32 is moved between its first and second positions by an actuator mechanism at 38. The actuator mechanism 38 is provided on a frame 40. More particularly, the actuator 38 consists of a pistol-type leaf spring grip 42 that is U-shaped and has a base 44, a fixed or stationary first leg 46 and a moving second leg 48. The first and second legs 46, 48, in their FIG. 1, orientation are pre-loaded to be biased away from each other. The body 16 extends rearwardly through the first and second legs 46, 48 and terminates in a threaded connection 50, which projects rearwardly through the leg 46.

The moving leg 48 is connected to a guide block 52 which translates guidingly in a fore and aft direction within a space 54 defined by the frame 40. The guide block 52 is in turn connected to the sleeve 32 so that the guide block 52 and sleeve 32 move in unison in a fore and aft direction.

The body 16, guide block 52, sleeve 32, and grip 42 are held removably in operative position on the frame 40 by front and rear holding caps 56, 58, respectively. The cap 58 holds the stationary grip leg 46 captively against the frame 40. By removing the caps 56, 58, the body 16, with the jaws 12, 14 thereon, and the sleeve 32 can be readily disassembled to facilitate cleaning and/or repair of the instrument 10.

In the FIG. 1 orientation for the instrument 10, the legs 46, 48, by reason of their being biased away from each other, urge the sleeve 32 forwardly to thereby normally place the jaws 12, 14 in a closed position. By holding the grip 42 in one hand, the user can squeeze the grip 42 to thereby draw the second leg 48 towards the first leg 46. The required movement of the leg 48 relative to the frame 40 is permitted by providing a guide slot 60 in the frame 40 for the leg 48. Rearward shifting of the leg 48 causes the guide block 52 and sleeve 32 to shift from right to left in FIG. 1 relative to the body 16 and jaws 12, 14 carried thereby. With sufficient gripping force applied, the sleeve 32 moves back to its first position in which the jaws 12, 14 are allowed to open.

To facilitate this gripping action, front and rear handle members 62, 64 are provided on the legs 46, 48, respectively. The front handle member 64 has finger recesses 65 for comfort and an integral, hollow sleeve 66 projecting rearwardly therefrom and defining a blind opening 68. The rear handle member 62 has a hand conforming recess 70 and an integrally formed, forwardly projecting sleeve 72 defining a blind opening 74. The sleeves 66, 72 are telescoped, one within the other and contain a coil spring 76 which acts between a rearwardly facing surface 78 on the handle member 64 and a forwardly facing surface 80 on the handle member 62. The spring 76 normally biases the second leg 48 away from the first leg 46 to thereby urge the sleeve 32 into its second position and bias the jaws 12, 14 closed with a force that augments the forward force applied to the sleeve 32 by the spring-loaded grip 42.

With the inventive structure, the user need only squeeze the grip 42 to open the jaws 12, 14, direct the needle 22 into the space 20 and thereby release the grip 42, whereupon the needle 22 is positively held in a closed operative position by the jaws 12, 14 under the combined spring force produced by the grip 42 and the spring 76.

The invention also comprehends the provision of structure to provide a still further gripping and locking force on the jaws 12, 14, which is accomplished through an outer sleeve 82, which surrounds and is concentric with the sleeve 32. A conventional luer lock 84 acts between the holding cap 56 and the outer sleeve 82. Through an actuator 86, the luer lock advances the sleeve 82 forwardly to thereby cause an inside surface 88 thereon to squeeze and/or lock the forward portions of the jaws 12, 14 to enhance the gripping force on the needle 22 beyond said first predetermined force applied through the sleeve 32. The sleeve 82 has an integrally formed, radially inwardly projecting bead 90 with annular ribs 92 thereon to mesh with ribs 94 on the jaws 12, 14 so that the advancing sleeve 82 makes ratchet-type engagement with the jaws 12, 14. This ratchet arrangement, however, is optional.

The invention contemplates other than a luer lock to advance the sleeve 82. A ratchet arrangement, for example, could be substituted for the luer lock 84 shown in FIG. 1.

A still further modification contemplated by the invention is to connect the luer lock 84 through suitable structure 96, known to those skilled in the art, to the sleeve 32, which thereby obviates the need for the outer sleeve 82. By then operating the luer lock 84, the sleeve 32 is caused to be advanced forwardly beyond its second position into a third position in which the jaws 12, 14 are squeezed by the sleeve surface 36 with a greater force than is imparted by the combination of the spring 76 and leaf spring grip 42. With this arrangement, the user can operate the grip 42 in the same fashion, pick up the needle 22, release the grip 42 to allow the jaws 12, 14 to hold the needle 22 through the combined force of the grip 42 and spring 76, and then operate the luer lock 84 to supplement the gripping force exerted by the jaws 12, 14.

Figure 3:
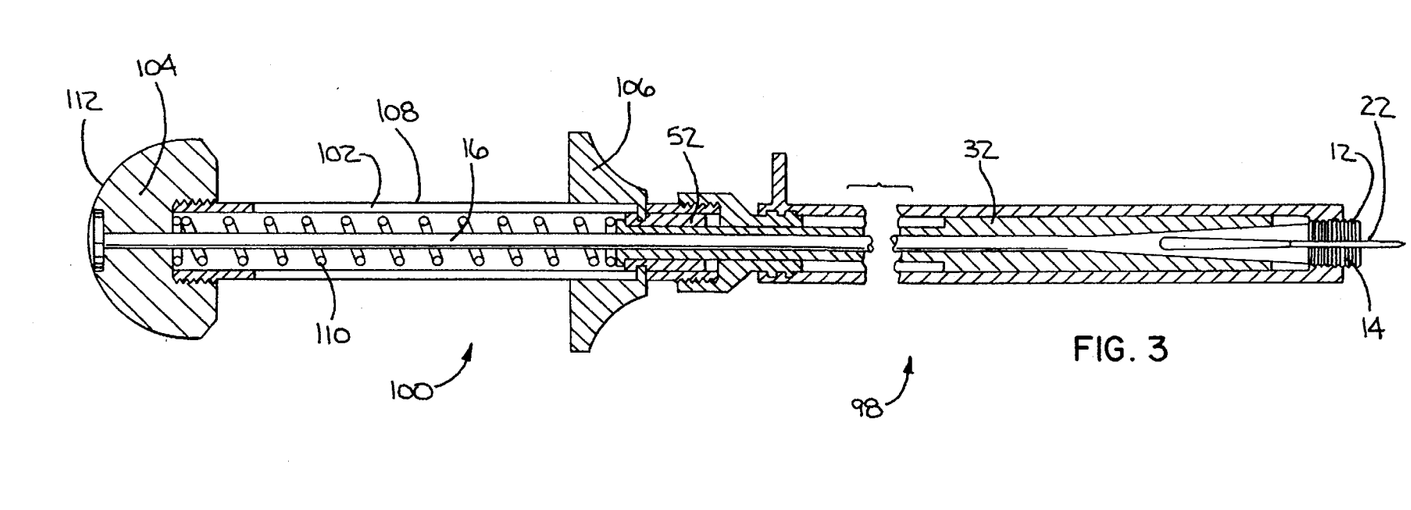
FIG. 3 is a sectional view of a modified form of surgical instrument for holding a needle according to the present invention.

A modified needle holding instrument, according to the present invention, is shown in FIG. 3 at 98. The principal difference between the instrument 98 and that 10 shown in FIGS. 1 and 2 is in the actuator mechanism at 100. The parts common to the instruments 10, 98 are numbered the same. The actuator mechanism 100 has a cylindrical frame 102 which supports a first member 104 attached to the body 16 and a second member 106 in the form of a disk which is slidable lengthwise guidingly along the outer surface 108 of the frame 102. The second member 106 connects to the guide block 52 so that the guide block 52 follows fore and aft movement of the second member/disk 106. A coil spring 110 acts between the first member 104 and guide block 52 to urge the guide block 52 and associated sleeve 32 to the second position therefor, corresponding to the closed position for the jaws 12, 14.

To operate the device, the user places the curved rear end 112 of the member 104 in the palm of the hand and with two adjacent fingers grasps the second member 106 and draws the member 106 towards the palm to thereby retract the sleeve 32 to its first position. The operation of the instrument 98 is otherwise the same as that 10 in FIGS. 1 and 2.

Figure 4:
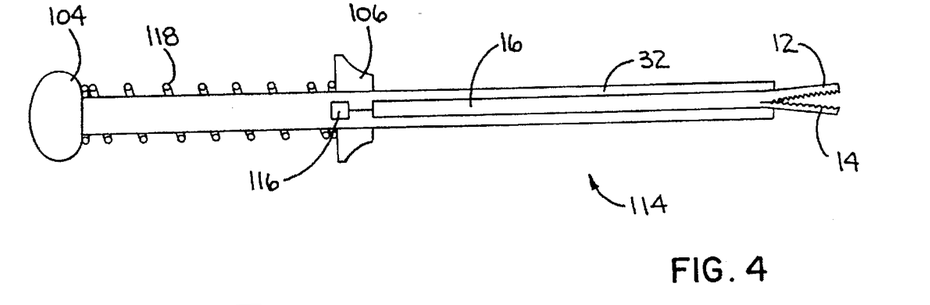
FIG. 4 is a schematic representation of a still further modified form of surgical instrument for holding a needle according to the present invention.

A still further modified form of needle holding instrument, according to the present invention, is shown at 114 in FIG. 4. The instrument 114 is modified from that 98 in FIG. 3 primarily by reason of the second member's 106 being operatively connected to the body 16 through structure shown schematically at 116. A coil spring 118 biases the second member 106 together with the body 116 and jaws 12, 14 forwardly relative to the sleeve 32 so that the jaws 12, 14 are normally in their open position. By drawing the second member 106 rearwardly towards the first member 104 in operation, the jaws 12, 14 are drawn into the sleeve 32 to effect closing of the jaws 12, 14. With this structure, the user must manually maintain a force between the members 104,106 to keep the jaws 14, 16, in their closed position.

Figure 5:
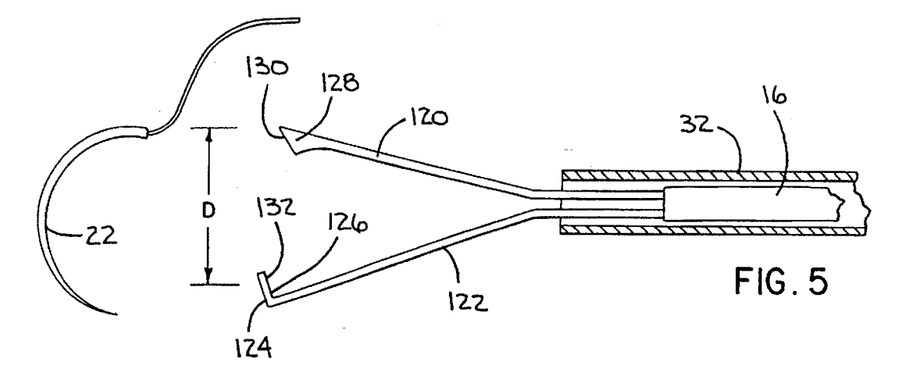
FIG. 5 is a fragmentary sectional view of a surgical instrument for holding a needle according to the present invention and showing a modified form of needle holding portion in an open position.
Figure 6:
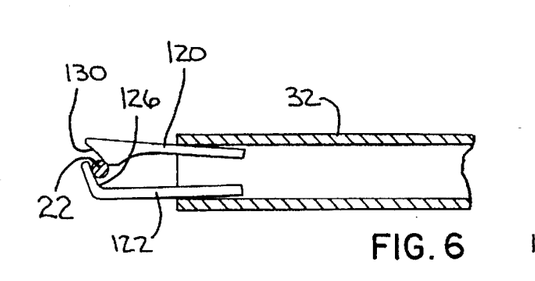
FIG. 6 is a view as in FIG. 5 with the jaws in a transition position.
Figure 7:
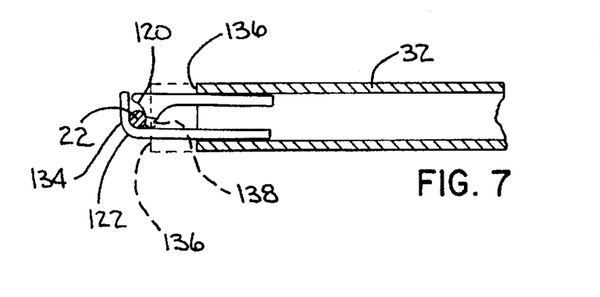
FIG. 7 is a view as in FIGS. 5 and 6 with the jaws in a closed position.

A modification to the jaws 12, 14, according to the invention, is shown in FIGS. 5–7. In FIGS. 5-7, cooperating jaws 120, 122 are made of spring-type material and are normally biased away from each other to an open position, shown in FIG. 5. The sleeve 32 is slidable lengthwise relative to the elongate jaws 120, 122 to thereby squeeze the jaws 120, 122 towards each other and ultimately into the closed position of FIG. 7.

To accommodate the needle 22, the jaw 122 has an L-shaped end 124 having a squared, curved, U-shaped or V-shaped surface 126 defining a seat for the needle 22. The surface 126 preferably opens rearwardly and radially inwardly.

The cooperating jaw 120 has a thickened end 128 defining a cam surface 130 which faces oppositely to the direction of opening of the surface 126 on the jaw 122 with the jaws 120, 122 closed. The cam surface 130 may be planar, or as shown in a preferred form, slightly concave, opening radially inwardly.

In operation, the offset end of the jaw 122 defines a pickup lip 132 that can be used to conveniently move under and pick up the needle 22 and guide it towards the surface/seat 126. By urging the sleeve 32 from right to left from its first position in FIG. 5 to its second position in FIG. 7, or by alternatively moving the jaws 120, 122, from left to right relative to the sleeve 32, the jaws 120, 122 are progressively squeezed together. At the transition position shown in FIG. 6, the cam surface 130 encounters the needle 22 and bears it captively against the surface 126. The cam surface 130 wedges the needle 22 against the surface 126 with a progressively increasing force in transition between the open and closed positions for the jaws 120, 122 until the needle 22 is firmly held in its operative position in the FIG. 7, closed positions for the jaws 120, 122. This construction is desirable in that a large range of needle size and shape can be accommodated.

It can be seen that with the depicted construction of the jaws 120, 122, the needle 22 is captured closely adjacent to the free end 134 of the jaw 122, which is the forwardmost projecting part of the instrument. In a preferred form, the jaws 120, 122, in their closed position of FIG. 7, and in the absence of a needle being held thereby, are drawn into the sleeve 32 on the order of 5 mm rearwardly from the forward sleeve edge 136. With this arrangement, the jaws 120, 122, as they are closed upon a needle, and withdrawn into the sleeve 32, forcibly bias the needle 22 against the sleeve forward edge 136. The needle 22 thus becomes positively trapped between the seat surface 126, the cam surface 130, and the sleeve forward edge 136. The needle 22, which is generally longer than the diameter of the sleeve 32 bridges the sleeve 32 at diametrically opposite locations, and is forcibly drawn thereagainst by the jaws 120, 122, which are rearwardly biased by the combined force produced by the grip 42, spring 76 and luer lock 84'.

Figure 7A:
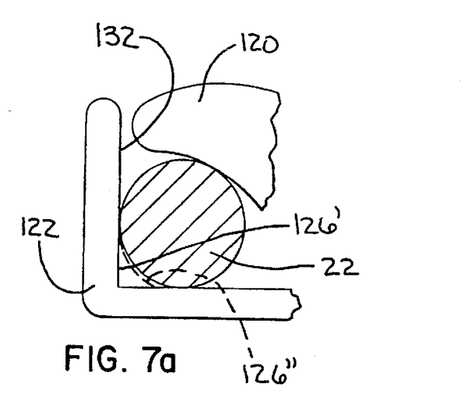
FIG. 7a is an enlarged, fragmentary, side elevation view showing the relationship of a needle to one of the jaws with the needle in the FIG. 7 position therefor.

FIG. 7a shows the relationship between the jaws 122 and needle 22 with two different configurations for the seat 126. The seat 126' is essentially square or V-shaped, while the seat 126", in phantom, is curved or U-shaped, to conform more closely to the contour of the needle 22. The needle 22 is thus prevented from canting by the front edge 136 of the sleeve 32 and is captively held cooperatively by the sleeve 32 and jaws 120, 122.

Another optional feature of the invention is to provide an extension 138 (FIG. 7) which abuts the jaw 122 with the jaws 120, 122 in the closed position therefor to thereby consistently relatively position the jaws 120, 122 in the closed position therefor.

Figure 8:
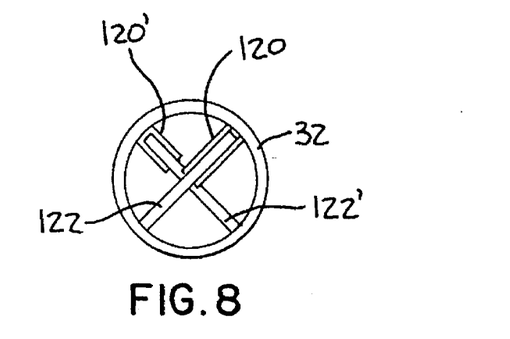
FIG. 8 is an enlarged end view of the surgical instrument in FIGS. 5–7.

A further modification to the invention is shown in FIG. 8. In FIG. 8, an additional jaw pair 120', 122' is shown arranged at right angles to the jaw pair 120, 122. The sleeve 32, upon being drawn back off of the jaws 120, 120', 122, 122', allows the jaws 120, 120', 122, 122' to open simultaneously. This allows the needle 22 to be picked up more readily without rotating the device through as much as 180°, as may be required with prior art structures,to allow the jaw 122 to engage and pick up the needle 22. With this construction, any needle residing within a circular area of a diameter D (FIG. 5) can be picked up without significant reorientation of the instrument.

In FIGS. 9 and 10, a prior art device is shown at 140 over which the present invention improves. The device 140 has an outer sleeve 142 and an inner sleeve 144. The inner sleeve 144 is slidable guidingly within the sleeve 142 and is biased from right to left by a spring member, shown schematically at 146. A pistol-type grip, shown schematically at 148, is used to draw the sleeve 144 back to the open position of FIG. 9.

The outer sleeve 142 has a cut-out 150 which defines a V-shaped, rearwardly opening seat 152 for the needle 22. The device 140 must be oriented to preliminarily place the needle 22 in the seat 152, after which the inner sleeve 144 is allowed to advance forwardly through the cut-out 150. An angled blocking edge 154 on the sleeve 144 progressively cuts off the depth of the seat 152 and thereby progressively wedges the needle 22 into the seat 152 until the closed position of FIG. 10 is realized.

With the needle 22 in the operative position of FIG. 10, the needle is supported on the outer sleeve 142 at diametrically opposite edges 156 so that the basic orientation of the needle 22 cannot be changed. One significant drawback is that the needle is situated a distance X (see FIG. 9) from the front edge 160 of the device 140. That portion 162 forwardly of the seat 152 thus interferes with the surrounding tissue during a suturing operation and prevents suturing in tight locations. Whereas with the present invention, it is possible to suture within 1–2 mm of a tissue in front of the instrument, the distance X (FIG. 9) is on the order of 5 mm.

Another problem with the device 140 is that it is very difficult to locate the needle 22 in the cut-out 150. A surgeon may have to blindly rotate and axially shift the device to seat the needle 22 in the cut-out 150. This may be difficult and time consuming as normal suturing operations require the repeated gripping, releasing, and re-gripping of the needle. To further aggravate this problem, the cut-out width in FIGS. 9 and 10 is small relative to the range of pickup for the inventive instrument.

The foregoing disclosure of specific embodiments is intended to be illustrative of the broad concepts comprehended by the invention.

I claim:

1. A surgical instrument for holding a needle, said instrument comprising:

a body;

first and second jaws integrally formed with said body and movable between a) an open position in which a needle can be directed between the jaws and b) a closed position in which a needle can be held in an operative position by the needle holding instrument; and means for selectively moving the jaws from said open position into said closed position, wherein said jaw moving means comprises a sleeve that is movable relative to and against at least one of said first and second jaws between first and second positions for moving the jaws between their open and closed positions, there being cooperating ribs on the sleeve and the at least one jaw to releasably maintain the jaws in their closed position.

2. The surgical instrument according to claim 1 wherein the sleeve surrounds at least a part of the body and first and second jaws and as an incident of the sleeve moving between its first and second positions the sleeve squeezes the jaws towards each other towards the closed position therefor.

3. The surgical instrument according to claim 1 wherein the jaws are normally biased to their open position.

4. The surgical instrument according to claim 1 including actuator means for moving the sleeve selectively between its first and second positions.

5. The surgical instrument according to claim 4 wherein said actuator means includes means for normally biasing the sleeve into one of said first and second sleeve positions.

6. The surgical instrument according to claim 4 wherein the actuator means includes a hand grip, said hand grip including a first member connected to the body and a second member connected to the sleeve, said second member being movable relative to the first member to thereby effect movement of the sleeve between its first and second positions.

7. The surgical instrument according to claim 6 wherein there is a spring member acting between said first and second members to thereby normally bias the jaws into one of said open and closed positions.

8. The surgical instrument according to claim 7 wherein the hand grip is a pistol-type grip defined by a U-shaped element with a base and spaced legs, said spaced legs defining said first and second members, said legs being graspable by the hand of a user and movable towards each other to thereby move the jaws into one of said open and closed positions.

9. The surgical instrument according to claim 8 wherein the legs are normally biased away from each other.

10. A surgical instrument for holding a needle, said instrument comprising:

a body;

first and second jaws on the body and movable between a) an open position in which a needle can be directed between the jaws and b) a closed position in which a needle can be held in an operative position by the needle holding instrument; and means for selectively moving the jaws from said open position into said closed position, wherein said jaw moving means comprises a sleeve that is movable relative to and against at least one of said first and second jaws between first and second positions for moving the jaws between their open and closed positions, there being means on the body for normally biasing the sleeve towards one of said first and second positions with a first predetermined force to thereby place the jaws in a closed position, there being selectively operable grip tightening means for increasing the biasing force on the sleeve above said first predetermined force to thereby increase a gripping force exerted by the jaws on a needle held in an operative position between the jaws.

11. A surgical instrument for holding a needle, said instrument comprising:

a frame;

an elongate body;

first and second jaws on the elongate body each having a flat surface over substantially their entire extent movable selectively towards and away from each other between (a) an open position in which a needle can be placed between the jaws and (b) a closed position in which the flat surfaces of the jaws can captively embrace a needle;

first means for normally biasing the jaws into their closed position with a first predetermined force;

second means for selectively biasing the jaws into their closed position with a force that is greater than the first predetermined force; and a first sleeve, said first means comprising means for moving one of the first sleeve and elongate body relative to the other of the sleeve and elongate body to close the jaws with said first predetermined force, said second means comprising means for moving the other of the first sleeve and elongate body relative to the one of the sleeve and elongate body to close the jaws with a force that is greater than the first predetermined force.

12. The surgical instrument according to claim 11 wherein the jaws are normally biased to one of their open and closed positions.

13. The surgical instrument according to claim 11 including actuator means to control said first and second means for moving the sleeve selectively between first and second positions.

14. The surgical instrument according to claim 13 wherein said actuator means includes means for normally biasing the sleeve into one of said first and second sleeve positions.

15. The surgical instrument according to claim 13 wherein the actuator means includes a hand grip, said hand grip including a first member connected to the frame and a second member connected to the sleeve, said second member being movable relative to the first member to thereby effect movement of the sleeve between its first and second positions.

16. The surgical instrument according to claim 15 wherein there is a spring member acting between said first and second members to thereby normally bias the jaws into one of said open and closed positions.

17. The surgical instrument according to claim 16 wherein the hand grip is a pistol-type grip defined by a U-shaped element with a base and spaced legs, said spaced legs defining said first and second members, said legs being graspable by the hand of a user and movable towards each other to thereby move the jaws into one of said open and closed positions.

18. The surgical instrument according to claim 17 wherein the legs are normally biased away from each other.

19. A surgical instrument for holding a needle, said instrument comprising:

first and second jaws movable selectively towards and away from each other between (a) an open position in which a needle can be placed between the jaws and (b) a closed position in which the jaws can captively embrace a needle;

first means for biasing the jaws into their closed position with a first predetermined force; and second means for selectively biasing the jaws into their closed position with a force that is greater than the first predetermined force, wherein the first means comprises a first sleeve that is movable between first and second positions, said sleeve in said second position surrounding at least a part of the first and second jaws and thereby squeezing the jaws to bias the jaws into their closed position with said first predetermined force, wherein said second biasing means includes a second sleeve, said first and second sleeves each having an axis, said sleeves being in axially overlapping relationship and said second biasing means includes means cooperating with the sleeve for selectively urging the second sleeve against at least one of the jaws to bias the jaws into their closed position with a force that is greater than the first predetermined force.

* * * * *